United States Patent [19]

Lock

[11] 3,978,266

[45] *Aug. 31, 1976

[54] SURGICAL DRESSINGS

[75] Inventor: Peter Maurice Lock, Gillingham, England

[73] Assignee: Ionics Lyo Products Company, Watertown, Mass.

[ * ] Notice: The portion of the term of this patent subsequent to Aug. 17, 1993, has been disclaimed.

[22] Filed: Sept. 13, 1973

[21] Appl. No.: 396,677

Related U.S. Application Data

[63] Continuation-in-part of Ser. No. 295,236, Oct. 5, 1972.

[30] Foreign Application Priority Data

Sept. 10, 1973 United Kingdom............... 46252/73

[52] U.S. Cl............................ 428/315; 260/2.5 AD; 260/2.5 AZ; 260/2.5 BD; 264/321; 260/54; 428/320
[51] Int. Cl.$^2$.......................................... C08G 18/14
[58] Field of Search................ 260/2.5 AD, 2.5 AZ, 260/2.5 BD; 264/321, 54; 161/159, 190; 428/315, 320

[56] References Cited

UNITED STATES PATENTS

| | | | |
|---|---|---|---|
| 3,012,283 | 12/1961 | Foster | 264/321 |
| 3,325,338 | 6/1967 | Geen | 264/321 |
| 3,328,505 | 6/1967 | Spencer | 264/321 |
| 3,370,117 | 2/1968 | Blue | 264/321 |
| 3,378,432 | 4/1968 | Spencer | 264/321 |
| 3,386,877 | 6/1968 | Skochdopole | 264/321 |
| 3,443,007 | 5/1969 | Hardy | 264/321 |
| 3,506,600 | 4/1970 | Zocco | 260/2.5 BD |
| 3,650,993 | 3/1972 | Zocco | 260/2.5 BD |
| 3,658,972 | 4/1972 | Ready | 264/321 |
| 3,763,301 | 12/1973 | Civardi | 264/321 |
| 3,816,233 | 6/1974 | Powers | 161/159 |

FOREIGN PATENTS OR APPLICATIONS

| | | |
|---|---|---|
| 1,065,994 | 4/1967 | United Kingdom |
| 1,253,845 | 4/1969 | United Kingdom |

Primary Examiner—C. Warren Ivy
Attorney, Agent, or Firm—Norman E. Saliba

[57] ABSTRACT

A foam material for use especially as a surgical dressing of the formula containing stannous octoate and a chlorofluoromethane and comprised of a polyether based polyurethane having a compressed dense surface which is absorbent to fluids as contrasted with the remaining uncompressed foam which is non-absorbent; the compressed dense surface containing foam cells which have only been partially collapsed as compared to the uncollapsed foam cells of the non-absorbent material.

8 Claims, No Drawings

SURGICAL DRESSINGS

This is a continuation-in-part of U.S. Pat. Application Ser. No. 295,236 filed on Oct. 5, 1972 in name of Peter Maurice Lock.

This invention relates to lyophilic polyurethane foam materials. Such materials have particular application as surgical dressings.

Dressing materials designed for wounds must have several properties; one is that a dressing should be absorbent to remove exudate from the wound and at the same time be capable of protecting the wound from injury as well as reducing the risk of infection thereof by harmful bacteria. Furthermore, wound dressing materials must be free of toxic substances which may be absorbed into the wound.

Known dressings, such as cotton lint, cotton wool pads or cotton/rayon wool pads faced with non-woven materials, have good absorbent qualities, but their surface fibres tend to adhere to the wound or to absorb the scab-forming serum so that they actually become embedded in the scab as it coagulates and hardens. Thus, if these dressings are removed to allow inspection and treatment of the wound, the wound tissue and/or the scab may be damaged thus retarding the healing process of the body or even re-opening the wound.

Attempts have been made to provide wound dressings of fully occlusive materials such as polythene and while such dressings provide a satisfactory skin regeneration environment in the vicinity of the wound, it is essential to apply them to a wound in a sterile state under sterile conditions to prevent harmful bacteria breeding close to or in the wound; this material does not absorb exudate satisfactorily, thus causing pooling in the wound which is not desirable.

Processes for subjection of polyurethane foams to heat and pressure are well known in the prior art. It is to be understood that the present invention does not claim as novel such processes in general, but rather provides a disclosure enabling certain polyurethane foams to be rendered lyophilic by application of a heat/pressure treatment.

An example of a prior art process for crushing a polyurethane foam, described in British Patent Specification No. 1,065,994, is one which comprises crushing the dry body of a polyurethane foam irreversibly at an elevated temperature, preferably between 300°F and 400°F and preferably under a pressure of 4 tons per square inch.

Such a process is not confined to foam cells adjacent a surface of the foam; one requirement which is specified is the necessity of heat the entire thickness of the foam to the required temperature range so as to obtain a predominate amount of crushed cells unlike the present invention in which heat may be applied directly to one surface. Furthermore, the product from the said process is intended for lamination to a textile material, for example, a woven or knitted material to provide a dimensional stabilizer while adding crease resistance and thermal insulation. The said specification makes no reference to the foam having any absorbent properties which is in accordance with the fact that such an application would require that the crushed foam product should not have lyophilic or absorbent characteristics. The above two factors distinguish the nature and function of the crushed foam of U.S. Pat. No. 1,065,994 from the present applicant's invention.

The prior art also provides examples of compressed polyurethane foams used for surgical dressings. One such example is the product described in British Patent Specification No. 1,253,845, which product comprises a substrate of one or more sheets of compressed cellular plastic material, the substrate having one face relatively more highly compressed than the other face, the less highly compressed face being provided with an adhesive. The less highly compressed face of that dressing is therefore intended for contact with the wound and the more highly compressed face is said to be substantially impermeable to water. Thus the compression taught by the above Patent has the effect of rendering the treated surface non-absorbent and is in contrast to the process of the present invention which renders the treated surface lyophilic.

A further example of a wound dressing prepared from compressed polyurethane foam is that described in U.S. Pat. No. 3,157,178, wherein the dressing comprises a body of elastic skeletonized plastic foam, the portion of the body for positioning adjacent a wound area being compressed to provide a shined surface for contact with a wound, said portion being only a small proportion of the thickness of said body. The product is however, substantially different to the product of the present invention. One of the primary objects of the above U.S. Pat. is to provide a dressing which will provide essentially free exposure of the wound to the air and to this end a "skeletonized" (or reticulated) foam is specified, that is a foam in which the membranes have been removed to a substantial extent, thereby leaving an open three dimensional skeletal structure. Furthermore, the prior patent teaches that the purpose of the denser membrane portion of the foam dressing is to provide a very smooth surface for contact with the wound, rather than to provide an absorbent surface. Indeed it is stated that because the foam is hydrophobic it must be made wettable, and this is accomplished by dipping the foam in a solution of a wetting agent. It is also stated (in column 5, lines 35–36) that the dense bottom layer on the dressing in fact helps the exudate from the wound not to penetrate the dressing too easily.

It will be seen therefore that the teaching of U.S. Pat. No. 3,157,178 is in contrast to the present invention in that the absorbency of the dressing is provided by treatment with a wetting agent; and the function of the compressed portion is to provide a smooth surface adjacent the wound and also a partial barrier to the absorption of exudate, whereas the dressing of the present invention is characterized by a lyophilic surface without the use of a wetting agent.

According to the present invention there is provided a polyurethane foam material the foam cells adjacent at least one surface of which are irreversibly partially collapsed relative to foam cells remote from said surface, said partially collapsed foam cells having the effect of rendering said surface lyophilic.

The foam cells adjacent said lyophilic surface have been defined as "irreversibly partially collapsed". It is known that polyurethane foam can be reversibly deformed or compressed to reduce the thickness up to a certain extent, but will substantially recover its original thickness upon washing or steam heating. The present invention relates to compression of the surface of the foam beyond this predetermined extent, that is to an "irreversible" process. The cells defined as "partially collapsed" have their wall members deformed to produce smaller cells, but it is important that the cells are not completely collapsed or fused. Such an effect is produced by controlling the heat/pressure/temperature parameters employed.

Very preferably a non-reticulated foam is utilized in the present invention, although experiments have shown that certain reticulated foams can be rendered lyophilic by appropriate selection of the heat/pressure/temperature parameters.

By the term "non-reticulated foam" is meant a foam consisting of numerous individual cells which are constructed of a three-dimensional skeletal structure formed by the intersecting cell wall members and of interconnected strands with the membranes or windows joined to the skeletal structure such that they partition adjacent cells. The skeletal structure in such foams is usually thicker than the membranes or windows. Conversely, by the term "reticulated foam" is meant one in which most or all of the membranes or windows are absent and substantially only the skeletal structure is present.

By the term "absorbent" is meant that the polyurethane foam will suck up, drink or take in aqueous based liquids in a manner and amount substantially similar to conventional cotton gauze or cotton wool wound dressings. In contrast, the term "non-absorbent" is meant a foam which is substantially hydrophobic and will not suck up, drink or take in aqueous based liquids.

The foam article of the present invention is preferably in the form of a sheet, strip or ribbon and both of the major surfaces thereof may be of increased density; where both surfaces of the foam are of increased density, the densities of the two surfaces may be of the same or different.

According to a further aspect of the present invention, there is provided a process for making a polyurethane foam material which comprises applying pressure and heat to a surface of a piece of polyurethane foam to irreversibly partially collapse the foam cells adjacent said surface to an extent such that said surface is rendered lyophilic. Said heat and pressure may be applied to said surface by means of a heated plate or roller or the surface may be subjected to a pressure step following a heat applying step. The heating step may be carried out using any suitable heating means such as for example infrared radiation or microwaves.

The surface of the foam which is to be treated is heated to a temperature not less than the softening point of the foam but less than the fusion temperature of the foam. This varies for different foams and the surface temperature of the foam may suitably be from 200°C to 300°C depending on the time it is subjected to the heat. Preferably the applied temperature is just below the fusion temperature of the foam and is desirably from 200°C to 270°C.

The applied pressure may for example be from almost 0 up 200 lbs/sq. in. and is preferably from 5 to 100 lbs./sq. in.

During the combined pressure and heat treatment a sheet of release material, for example paper treated with silicones, may be placed between the heating means and the surface of the foam to prevent adhesion of the foam material to the plate of roller. In a treatment in which pressure is applied after the foam has been treated the release material may be employed only for the pressure application.

The initial piece of foam may be of any suitable thickness but is preferably from 1cm to 10cm in thickness and is preferably modified by heat and pressure to a final thickness of from 0.5cm to 5cm, preferably with a compressed lyophilic surfce thickness of up to 5mm. To obtain the desired lyophilic result, the foam material is usually reduced to about half its original thickness. However, this is not essential; very thin pieces of foam material approximately 3mm thickness can be made lyophilic by this process and it is only necessary to modify the surface to a depth of say 0.4mm to achieve a satisfactory result.

The foam sheet, strip or ribbon may be similarly modified on both faces for which purpose the foam after being removed from between the plate or roller and the release coated paper (if present) is reversed and the operation is repeated. Alternatively the pressure plate may be heated to a foam modifying temperature so that both surfaces of the foam or even the full thickness of the foam may be modified by heat and pressure in one or more pressing and heating operations.

The foam articles of the present invention are particularly advantageous for use as surgical dressing materials. In this respect, the product can be readily sterilized, for example, by means of a steam autoclave, gamma radiation, ethylene oxide. Also the body of the dressing material is suitable for incorporating a medicament, such as an anti-bacterial and/or antiseptic. The dressing is impregnated with such a medicament after the heat/pressure/treatment but prior to any sterilization process. The dressing may be treated by depositing a film of medicated material on to the dressing or by dipping the dressing into a solution of medication material and then drying the material.

The foam which is employed in the invention may be a polyurethane foam based on polyester or based on polyether. However, not all foams within this definition produce the desired lyophilic result. The applicant has attempted to determine a physical or chemical characteristic which may predict that a particular polyurethane foam will be rendered lyophilic. It is thought that the presence of the foam of stannous octoate and trichlorofluoromethane is important although the invention is not limited to this feature. In general it is necessary to test each given sample of foam, but two preferred formulations of foam are set out below in the Examples. The density, cell size and weight of the initial foam material may be chosen for the particular application for which the lyophilic product is required.

It has been found that all samples of foams which have been tested do not produce a lyophilic result. It is likely that the shape and structure of the cells in the foam are important. The heat and pressure treatment of the foam has the effect of causing the foam cells to coalesce to give the surface region of the foam the quality of being sufficiently occlusive to engender body healing processes and yet being sufficiently absorptive that it can absorb serum exuding from the wound.

From a further aspect the present invention provides a method of treating wounds in mammals which method comprises applying to the wound a surgical dressing of the present invention.

Amongst possible applications of the surgical dressing material of the present invention, there may be mentioned simple wound-dressings, post-operative wound dressings, adhesive plaster dressings, and swabs for general and medical use.

It is envisaged that, for application as an adhesive plaster dressing, the material would be produced with a thin plastics film laminated to one side thereof and on the other side of the material an adhesive layer protected by a strippable sheet.

Swabs made from the material may be rendered radio-opaque by impregnation thereof by a radio-opaque agent such as, for example, barium sulphate or iodine extractive or by any other suitable technique.

Further applications for the material of the present invention exist, such as, foam bandages to replace crepe and conforming bandages, foam eye pads to replace conventional gauze and wool pads, foam adhesive sheets to replace felt and other orthopaedic paddings, foam pressure-relief pads, foam dressing packs for use in the treatment of varicose veins by the injection technique, impregnated dressings, foam positioning sets, foam face masks and foam preparation swabs.

The material also has applications in many fields other than medicine. It has been found, for example, that material according to the present invention is excellent for for removal of condensation from windows or the like or for mopping up moisture from articles such as crockery, glassware, cars, floors.

A further envisaged use for the material according to this invention is as a light-weight body-insulative material capable of absorbing large quantities of perspiration.

The preparation and properties of surgical dressing materials according to the present invention are illustrated by the following Examples:

EXAMPLE 1

A block of polyurethane foam based on polyether was manufactured from the following formulation of ingredients (parts by weight):

| | |
|---|---|
| polyoxypropylene glycol (marketed by Lankro Chemicals Ltd under the name "PROPYLAN 8123") | 100 parts |
| stannous octoate (marketed under the name "NUOCURE 28" by Durham Raw Materials Limited) | 0.25 parts |
| water | 4.00 parts |
| dimethylethanolamine (marketed under the name "PROPAMINE A" by Lankro Chemicals Ltd) | 0.50 parts |
| silicone oil (marketed by Union Carbide under the name "L.520" | 200 parts |
| trichlorofluoromethane (marketed by Du Pont (UK) Ltd., under the name "FREON 11" | 15 parts |
| 80-20 toluene di-isocyanate (marketed under the name "HYLENE TM" by Du Pont (UK) Limited) | 82.50 parts |

A sheet of foam was cut from the block in conventional manner. A piece of silicone-treated release paper was placed on one surface of the sheet and this was placed in contact with a metal plate heated to a temperature of 205°C. A pressure plate was forced against the free face of the foam, to press it against the heated plate. A pressure of 70 lbs/sq. in. was maintained for about 20 seconds, the pressure plate removed and the sheet of modified foam was stripped from the silicone paper.

EXAMPLE 2

The procedure of Example 1 was repeated using a foam manufactured from the following formulation (parts by weight):

| | |
|---|---|
| Polyoxypropylene glycol (M.W. 3,000; "NIAX", Union Carbide) | 100 parts |
| Stannous octoate ("Nuocure 28", Durham Raw Materials Ltd) | 0.4 parts |
| Water | 2.8 parts |
| Dimethylethanolamine ("Propamine A", Lankro Chemicals ltd) | 0.7 parts |
| Silicone Oil (Union Carbide) | 1.6 parts |
| Trichlorofluoromethane ("Freon 11", Du Pont (UK) Ltd) | 13.0 parts |
| Toluene di-isocyanate 80/20 (405 Index "Hylene TM", Du Pont (UK) Limited) | 36.9 parts |

A dressing prepared according to either Example 1 or 2 has numerous advantages and desirable features, amongst which may be mentioned the following:

a. The dressing speeds up the healing process.
b. The dressing is very soft and therefore causes little or no discomfort to a patient.
c. The dressing can conform to virtually any anatomical contour and, therefore, ensure an even distribution of pressure over the skin surface of a patient.
d. The resilience of the dressing enables continuous contact with a wound, contusion, swelling or the like to be maintained even in the case where swelling or oedema subsides.
e. All exudates from the injured tissue are carried into the foam from the lyophilic surface thereof, thereby leaving said surface in a soft and pliant state.
f. The dressing has desirable non-adhesive properties which simplify the removal of dressings and the inspection of the skin surface.
g. The dressing is X-ray transparent and can therefore be left in situ while X-ray inspection of the wound, injury or the like takes place.
h. The dressing can be used as a haemostatic dressing.
i. The ability of the dressing to accommodate generous amounts of blood and/or exudate, allows the dressing to remain on the affected site for longer than is the case with conventional dressings.
j. The dressing will not support bacterial growth.

Effects of dressings on standard shallow wounds in Pig Skin

In Examples 3 and 4, tests were performed on two dressings:
Dressing A : prepared as in Example 1
Dressing B : As Dressing A, but with the second surface of the foam modified, also by the method as described in Example 1.

EXAMPLE 3

Twelve standard shallow wounds were made in the skin on the back of a young female large white pig. Six wounds were covered with dressing A (one surface only modified — placed next to the wound) and six with dressing B (both surfaces modified by heat and pressure).

One dressing of each type was removed at 2, 4 and 7 days to assess the state of the wound clinically.

Biopsy specimens were taken from the wounds with dressings in place and from wounds from which dressings had been removed at each time interval.

Results

Clinical Assessment 2 days — blood and exudate had penetrated into dressings and was well dispersed and dry. The wound surface was still moist and the dressings were non adherent.

4 days — A serous scab had formed in the dressing immediately above the wound surface. Wounds appeared level and clean.

7 days — Dressings peeled off without damage to wounds which had a dry clean, healed surface.

Histological Assessment

The wound surface appears to have been moist during the period of epidermal regeneration. The bulk of the exudate was absorbed into the dressing. The wounds have healed rapidly and the new epidermis is well differentiated. The surface of the wound is smooth and level.

Measurements of the speed of epidermal regeneration

Extent of wound surface covered by new epidermis

| Dressing removed | Dressing A | Dressing B |
|---|---|---|
| 2 days | 32% | 45% |
| 4 days | 84% | 52% |
| 7 days | 100% | 100% |

| Dressing in place | Dressing A | Dressing B |
|---|---|---|
| 2 days | 40% | —* |
| 4 days | 98% | 99% |
| 7 days | 100% | 99% |

*Specimens damaged during processing

EXAMPLE 4

Six standard shallow wounds were covered with Dressing A and biopsy specimens of the wounds with the dressings intact were obtained after 72 hours for measurements of epidermal regeneration.

Extent of wound surface covered by new epidermis

| Dressing in place 3 days | Dressing A |
|---|---|
| Wound 1 | 97% |
| Wound 2 | 98% |
| Wound 3 | 95% |
| Wound 4 | 100% |
| Wound 5 | 89% |
| Wound 6 | 94% |
| Average | 96% |

This result, 96% of the wound surface covered by new epidermis at three days, compares with a norm of 38% of wounds healed without dressings and 92% for wounds covered with polythene film. There is thus an extremely high rate of epithelialisation.

I claim:

1. An integrally formed, non-laminated, non-rigid, open celled polyurethane foam wound dressing material comprising a foam based on a polyether formulation employing stannous octoate and a chlorofluoromethane wherein at least one of the surfaces of said material consists of a surface layer having a density substantially greater than the remaining portions of the said foam material; said dense surface layer being absorbent to aqueous based liquids in a manner and amount substantially similar to conventional cotton gauze or cotton wool wound dressings and comprised of open foam cells which are irreversibly partially collapsed as contrasted to the foam cells of said remaining portions of the material which are substantially uncollapsed and non-absorbent to aqueous based liquids.

2. A material as claimed in claim 1, wherein the original foam is manufactured from a formulation comprising the following composition by weight:

| | |
|---|---|
| Polyoxypropylene glycol | 100 parts |
| Stannous octoate | 0.2–0.3 parts |
| Water | 1–10 parts |
| Dimethylethanolamine | 0.1–1.0 parts |
| Silicone oil | 1–10 parts |
| Trichlorofluoromethane | 10–20 parts |
| Toluene di-isocyanate | 70–90 parts. |

3. A material as claimed in claim 1, wherein the original foam is manufactured from a formulation comprising the following composition by weight:

| | |
|---|---|
| Polyoxypropylene glycol | 100 parts |
| Stannous octoate | 0.1–1.0 parts |
| Water | 1–10 parts |
| Dimethylethanolamine | 0.1–1.0 parts |
| Silicone oil | 1–10 parts |
| Trichlorofluoromethane | 10–20 parts |
| Toluene di-isocyanate | 25–50 parts. |

4. An article having a surgical or moisture-absorbing application, which comprises a polyurethane foam material as claimed in claim 1.

5. A swab which comprises a polyurethane foam material as claimed in claim 1.

6. A swab as claimed in claim 5, which constitutes a medical swab.

7. A swab as claimed in claim 5, which constitutes a floor swab.

8. A light-weight thermally-insulative material capable of absorbing perspiration, which comprises a polyurethane foam material as claimed in claim 1.

* * * * *